United States Patent
Christensen

(10) Patent No.: US 6,805,717 B2
(45) Date of Patent: Oct. 19, 2004

(54) ENERGY-STORING PROSTHETIC FOOT WITH ELONGATED FOREFOOT

(75) Inventor: Roland J. Christensen, Fayette, UT (US)

(73) Assignee: Roland J. Christensen, as operating Manager of RJC Development, LC, General Manager of the Roland J. Christensen Family Limited Partnership, Fayette, UT (US)

( * ) Notice: Subject to any disclaimer, the term of this patent is extended or adjusted under 35 U.S.C. 154(b) by 55 days.

(21) Appl. No.: 10/268,015

(22) Filed: Oct. 8, 2002

(65) Prior Publication Data

US 2004/0068328 A1 Apr. 8, 2004

(51) Int. Cl.[7] ............................... A61F 2/66; A61F 2/64
(52) U.S. Cl. ........................................... 623/52; 623/47
(58) Field of Search ...................................... 623/47–56

(56) References Cited

U.S. PATENT DOCUMENTS

| | | |
|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 6/1958 | Mauch |
| 3,551,914 A | 1/1971 | Woodall |
| 3,871,032 A | 3/1975 | Karas |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,506,395 A | 3/1985 | Haupt |
| 4,547,913 A | 10/1985 | Phillips |
| 4,645,509 A | 2/1987 | Poggi et al. |
| 4,676,801 A | 6/1987 | Lundeen |
| 4,721,510 A | 1/1988 | Cooper et al. |
| 4,822,363 A | 4/1989 | Phillips |
| 4,865,611 A | 9/1989 | Al-Turaiki |
| 4,938,775 A | 7/1990 | Morgan |

(List continued on next page.)

FOREIGN PATENT DOCUMENTS

| | | |
|---|---|---|
| DE | 295807 | 12/1916 |
| GB | 1550-658 | 8/1979 |
| IT | 556381 | 11/1958 |
| RU | 2033772 | 4/1995 |
| SU | 560606 | 7/1977 |

Primary Examiner—Alvin Stewart
(74) Attorney, Agent, or Firm—Thorpe North & Western

(57) ABSTRACT

A prosthetic foot device includes an ankle section with a discrete, straight section in a substantially vertical orientation with a curved section on both sides. An attachment member can be coupled to a limb of an amputee. An elongated forefoot portion can have an upper attachment section attached to the attachment member, and can extend downwardly through the ankle section positioned at an ankle location of a natural foot, and forwardly through an arch section, to a toe section positioned at a toe location of a natural foot. The first curved section can interconnect the attachment section and the straight section, while the second curved section can interconnect the straight section and the arch section.

26 Claims, 3 Drawing Sheets

U.S. PATENT DOCUMENTS

| | | | |
|---|---|---|---|
| 4,959,073 | A | 9/1990 | Merlette |
| 5,019,109 | A | 5/1991 | Voisin |
| 5,030,239 | A | 7/1991 | Copes |
| 5,037,444 | A | 8/1991 | Phillips |
| 5,112,356 | A | 5/1992 | Harris et al. |
| 5,116,383 | A | 5/1992 | Shorter et al. |
| 5,116,384 | A | 5/1992 | Wilson et al. |
| 5,181,932 | A | 1/1993 | Phillips |
| 5,181,933 | A | 1/1993 | Phillips |
| 5,217,500 | A | 6/1993 | Phillips |
| 5,290,319 | A | 3/1994 | Phillips |
| 5,376,133 | A | 12/1994 | Gramnas |
| 5,376,141 | A | 12/1994 | Phillips |
| 5,387,246 | A | 2/1995 | Phillips |
| 5,425,781 | A | 6/1995 | Allard et al. |
| 5,425,782 | A | 6/1995 | Phillips |
| 5,443,528 | A | 8/1995 | Allen |
| 5,443,529 | A | 8/1995 | Phillips |
| 5,458,656 | A | 10/1995 | Phillips |
| 5,464,441 | A | 11/1995 | Phillips |
| 5,482,513 | A | 1/1996 | Wilson |
| 5,486,209 | A | 1/1996 | Phillips |
| 5,507,838 | A | 4/1996 | Chen |
| 5,509,936 | A | 4/1996 | Rappoport et al. |
| 5,509,938 | A | 4/1996 | Phillips |
| 5,514,185 | A | 5/1996 | Phillips |
| 5,514,186 | A | 5/1996 | Phillips |
| 5,549,714 | A | 8/1996 | Phillips |
| 5,571,210 | A | 11/1996 | Lindh |
| 5,571,213 | A | 11/1996 | Allen |
| 5,593,455 | A | 1/1997 | Phillips |
| 5,593,456 | A | 1/1997 | Merlette |
| 5,593,457 | A | 1/1997 | Phillips |
| 5,653,767 | A | 8/1997 | Allen et al. |
| 5,725,598 | A | 3/1998 | Phillips |
| 5,728,175 | A | 3/1998 | Rincoe |
| 5,728,176 | A | 3/1998 | Phillips |
| 5,728,177 | A | 3/1998 | Phillips |
| 5,766,265 | A | 6/1998 | Phillips |
| 5,769,896 | A | 6/1998 | Rosendahl et al. |
| 5,776,205 | A | 7/1998 | Phillips |
| 5,779,735 | A | 7/1998 | Molino |
| 5,800,565 | A | 9/1998 | Biedermann |
| 5,800,569 | A | 9/1998 | Phillips |
| 5,824,112 | A | 10/1998 | Phillips |
| 5,888,238 | A | 3/1999 | Phillips et al. |
| 5,893,891 | A | 4/1999 | Zahedi |
| 5,899,944 | A | 5/1999 | Phillips |
| 5,976,191 | A | 11/1999 | Phillips |
| 5,993,488 | A | 11/1999 | Phillips |
| 6,019,795 | A | 2/2000 | Phillips |
| 6,071,313 | A | 6/2000 | Phillips |
| 6,165,227 | A | 12/2000 | Phillips |
| 6,206,934 | B1 | 3/2001 | Phillips |
| 6,254,643 | B1 | 7/2001 | Phillips |
| 6,261,324 | B1 | 7/2001 | Merlette |
| 6,280,479 | B1 | 8/2001 | Phillips |
| 6,290,730 | B1 | 9/2001 | Pitkin et al. |

ENERGY-STORING PROSTHETIC FOOT WITH ELONGATED FOREFOOT

BACKGROUND OF THE INVENTION

1. Field of the Invention

The present invention relates generally to prosthetic feet. More particularly, the present invention relates to resilient, energy-storing prosthetic feet with an elongated forefoot.

2. Related Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward.

In addition, the performance of these energy storing feet has been altered in various ways, such as by using multiple springs in various configurations, using bladders or resilient materials disposed between various elements, and using multiple springs that deflect at different intervals of foot deflection to add resistance.

As described above, such energy-storing prosthetic feet typically have either a J-shape or a C-shape configuration or profile with broad, continuous curvatures. The length of a J-shaped foot is limited in the vertical direction by the length of the residual limb of the amputee. Similarly, the length of a C-shaped foot is limited in the vertical direction by the length of the residual limb of the amputee, and in the horizontal direction by the typical size of a natural foot. It will be appreciated that the shape and dimensions of the foot can affect or limit the performance or bending characteristics of the foot.

SUMMARY OF THE INVENTION

The continued development of improved prosthetic feet is an ongoing goal. It has been recognized that it would be advantageous to develop a prosthetic foot that maximizes the length of an energy-storing member to provide greater energy storage and release, and improved cushion or spring characteristics.

The invention provides a prosthetic foot device with a discrete, straight ankle section with curved sections on both sides to allow extra length to store and return energy during use, to contribute to extra spring or cushion of the foot, and to improve vertical shock resistance. The foot device can include an attachment member coupled to a limb of an amputee, and an elongated forefoot portion. The forefoot portion can extend 1) rearwardly through an upper attachment section attached to the attachment member, 2) downwardly through an ankle section positioned at an ankle location of a natural foot, and 3) forwardly through an arch section, 4) to a toe section positioned at a toe location of a natural foot. The ankle section can include a discrete, straight section oriented substantially vertically. A first curved section can interconnect the attachment section and the straight section, while a second curved section can interconnect the straight section and the arch section.

In accordance with a more detailed aspect of the present invention, the foot device can further include a lower footplate attached to the upper forefoot portion. The footplate can have a toe section positioned at a toe location of a natural foot, and can extend rearwardly through an arch section to a heel section positioned at a heel location of a natural foot.

In accordance with another more detailed aspect of the present invention, the ankle section of the forefoot portion can be positioned at a rearmost location of the foot device, and over the heel section of the lower footplate. Thus, the forefoot portion can be further elongated to store and return energy during use, to contribute to extra spring or cushion of the foot, and to improve vertical shock resistance.

In accordance with another more detailed aspect of the present invention, the foot device can further include an elongated heel portion attached to the upper forefoot portion. The heel portion can have an attachment section attached to the upper forefoot portion, and can extend rearwardly to a heel section positioned at a heel location of a natural foot.

In accordance with another more detailed aspect of the present invention, the forefoot portion, the footplate, and/or heel portion can be flexible to store energy and resilient to return energy. The forefoot portion, the footplate, and/or heel portion can include a composite material with fiber in a resin matrix.

In accordance with another more detailed aspect of the present invention, the forefoot portion, the footplate, and/or heel portion can include at least two laterally separated and adjacent portions.

In accordance with another more detailed aspect of the present invention, the foot device can have an oblique attachment. The attachment member can have a lower oblique surface. The attachment section can have an upper oblique attachment surface attached to the lower oblique surface of the attachment member.

Additional features and advantages of the invention will be apparent from the detailed description which follows, taken in conjunction with the accompanying drawings, which together illustrate, by way of example, features of the invention.

DETAILED DESCRIPTION

Figure 1A:
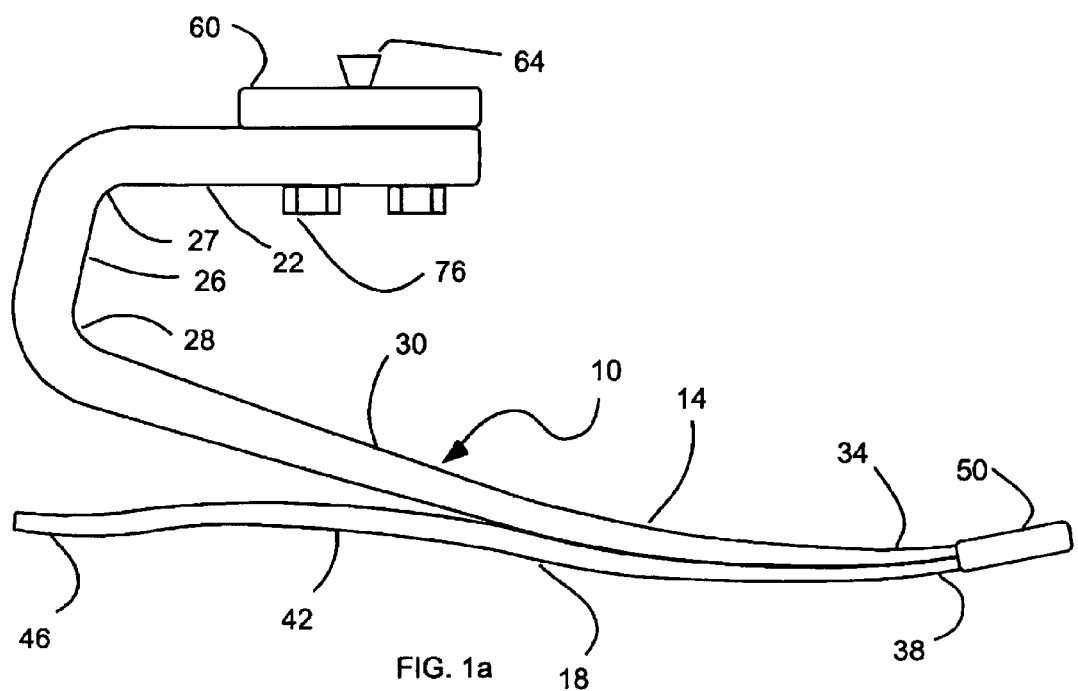
FIG. 1*a* is a side view of a prosthetic foot in accordance with an embodiment of the present invention.
Figure 1B:
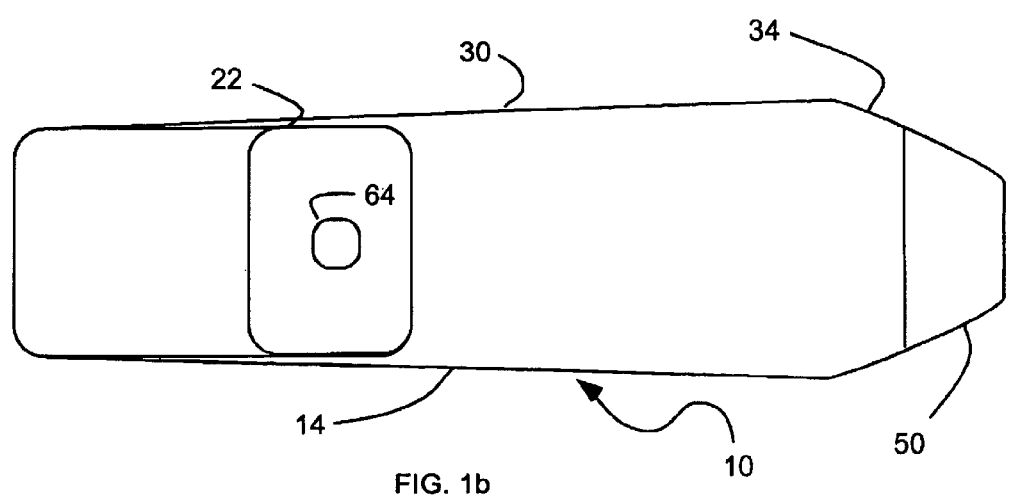
FIG. 1*b* is a top view of the prosthetic foot of FIG. 1*a*.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1a and b, a prosthetic foot, indicated generally at 10, in accordance with the present invention is shown. The foot 10 can include an elongated, upper forefoot portion or forefoot 14, and a lower footplate 18. The forefoot portion 14 can include an upper attachment section 22 to be coupled to a limb of an amputee. The forefoot portion 14 can extend rearwardly through the attachment section 22, downwardly through an ankle section 26, forwardly through an arch section 30, and to a toe section 34. The ankle section 26 is positioned at an ankle location of a natural foot. Likewise, the toe section 34 is positioned at a toe location of a natural foot. The toe location is a region near the forward end of the foot where toes of a natural foot would be located.

The ankle section 26 of the forefoot portion 14 can include a discrete, straight section that is oriented substantially vertically. A first curved section 27 can interconnect the attachment section 22 and the ankle section 26. Similarly, a second curved section 28 can interconnect the ankle section 26 and the arch section 30. Thus, the ankle section 26 can include the discrete, straight section intermediate two curved sections 27 and 28. The forefoot portion 4 thus can extend 1) rearwardly and/or downwardly through the attachment section 22, 2) rearwardly and downwardly through the first curved section 27, 3) downwardly through the straight section or ankle section 26, 4) downwardly and forwardly through the second curved section 28, 5) forwardly and/or downwardly through the arch section 30, and 6) to the toe section 34.

The discrete, straight section is distinct from the first and second curved sections 27 and 28. The discrete, straight section can be elongated and can have a length longer than either of the first and second curved sections 27 and 28. The discrete, straight section can be distinguishable and distinct from the curved sections 27 and 28 because it is straight and elongated with respect to the curved sections. Thus, the ankle section 26 can have a curvature or shape that is discontinuous.

The forefoot portion 14 or ankle section 26 can form a substantially block C-shape that is vertically oriented. The forefoot portion or ankle section forms a spring portion that can bend and flex. The discrete straight section of the ankle section 26 allows the forefoot portion 14 to be longer, and thus to store and return more energy during use, contributes to extra spring or cushion of the foot, and improves vertical shock resistance.

The lower footplate 18 can be attached to the upper forefoot portion 14, and disposed under the upper forefoot portion 14. The lower footplate 18 can extend rearwardly through a toe section 38, through an arch section 42, and to a heel section 46. The toe section 38 is positioned at a toe location of a natural foot. Likewise, the heel section 46 is positioned at a heel location of a natural foot. The heel location is a region near the rearward end of the foot where the heel of a natural foot would be located. The toe section 38 of the lower footplate 18 can be attached to the toe section 34 of the upper forefoot portion 14. The attachment 50 can be formed by wrapping the toe sections 34 and 38 with fibers in a resin matrix.

The ankle section 26 of the forefoot portion 14 can be positioned at a rearmost location of the foot device 10, and over the heel section 46 of the lower footplate 18. Thus, the forefoot portion 14 extends from the toe section 34 at the front of the foot, to above the heel section 46 at the rear of the foot. Thus, the forefoot portion 14 can be further elongated to store and return energy during use, to contribute to extra spring or cushion of the foot, and to improve vertical shock resistance.

The foot 10 also can include an attachment member 60 to attach the upper forefoot portion 14 to a socket configured for the specific needs of the amputee. Such sockets typically have a portion adapted for standard attachment. The attachment member 60 can include a pyramid connector 64 on a top end or upper surface, as is well known in the art to connect to a socket on the stump of the amputee. The attachment section 22 can be coupled to the attachment member 60 by fasteners, such as bolts 76. For example, the bolts 76 can extend through apertures in the attachment section 22 of the forefoot portion 14 and into threaded bores in the attachment member 60. It is of course understood that any type of fastener or connection can be used, including for example, screws, clips, etc.

Figure 2:
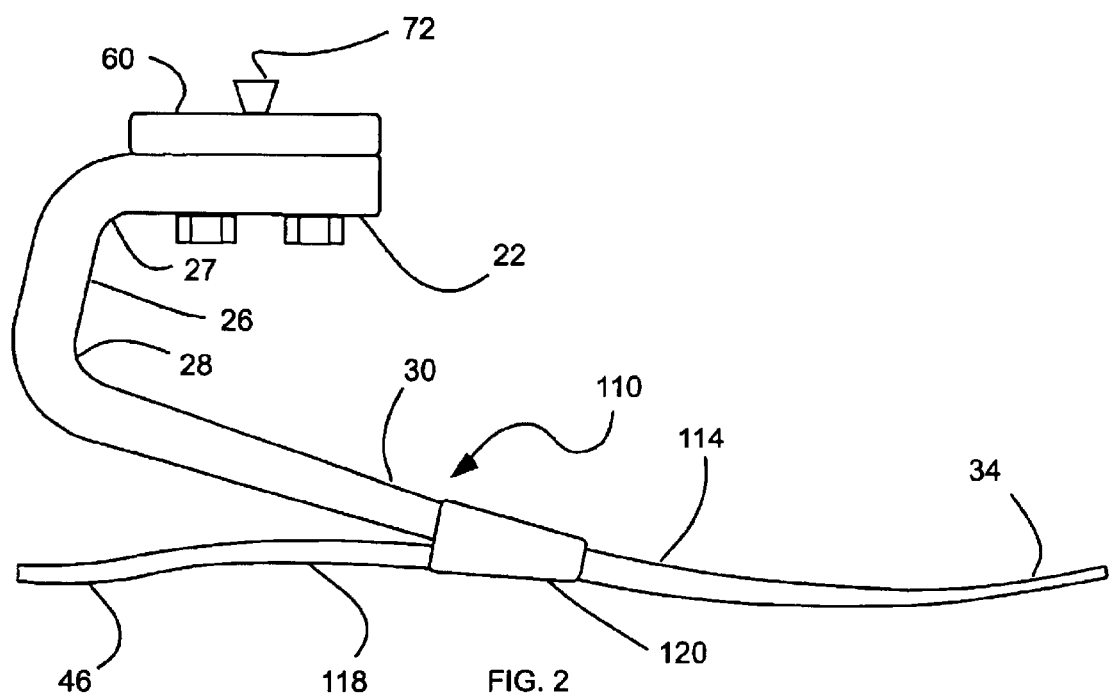
FIG. 2 is a side view of a prosthetic foot in accordance with an embodiment of the present invention.
Figure 3:
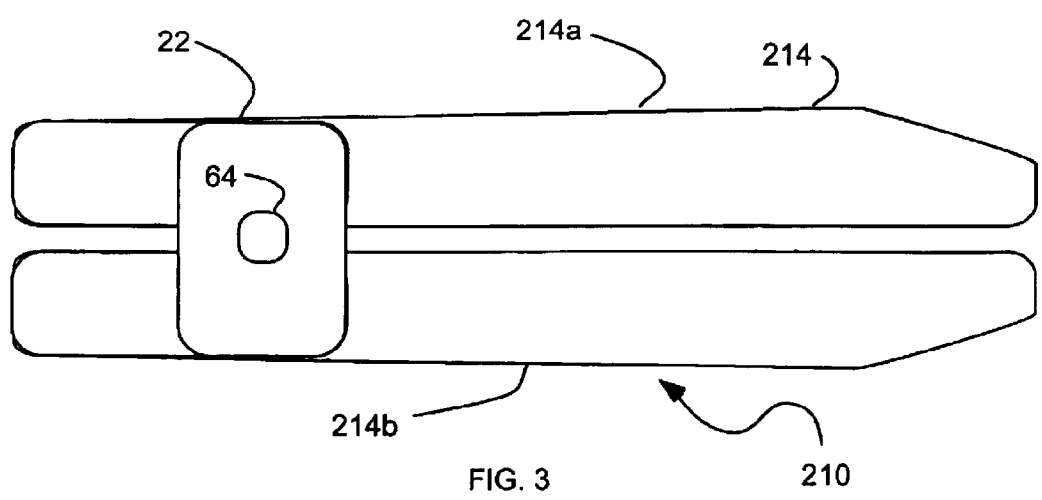
FIG. 3 is a top view of a prosthetic foot in accordance with an embodiment of the present invention.

In addition, the pyramid connector 64 can be moved fore or aft, or forward or rearward, to change the bending characteristics of the forefoot portion 14 or foot 10. In one aspect, the pyramid connector 64, or other connector, can be positioned at approximately the first third of the foot 10, with respect to, or measured from, the rearmost of the foot, as shown in FIGS. 1a and b. Alternatively, the connector can be positioned at approximately the first quarter, as shown in FIGS. 2 and 3. Positioning the connector at the first third provides a longer lever arm to store and return energy during use, contributes to extra spring or cushion of the foot, and improves vertical shock resistance.

The entire foot 10, or the upper forefoot portion 14 and lower footplate 18, can be an energy-storing member that flexes and bends under a load to store energy, and returns while the load is released to release the stored energy. The forefoot portion 14 and footplate 18 can include or be formed of a flexible and resilient material. For example, the material can be a composite with fibers disposed in a resin matrix. The fiber can be disposed in unidirectional, mat or weave with several layers. As the amputee steps, or pivots forward, on the prosthetic foot 10, the forefoot portion 14 deflects. Because the forefoot portion 14 is made of a resilient material, the forefoot portion 14 acts as a spring, and stores the energy to be released as the user moves forward. Similarly, as the user steps on the footplate 18, the footplate deflects and stores energy to be released as the amputee pivots forward.

Referring to FIG. 2, another prosthetic foot 110 is shown that is similar in many respects to the foot described above. The foot 110 can include an upper forefoot portion 114, similar to that above, and a heel portion 118. The heel portion 118 can have an attachment section 120 attached to the arch section 30 of the upper forefoot portion 114, and extending rearwardly to a heel section 46 positioned at a heel location of a natural foot. The attachment can be formed by wrapping the attachment section 120 of the heel portion 118 and the arch section 30 of the upper forefoot portion 114 with fibers in a resin matrix. As above, the forefoot and heel portions 114 and 118 can be energy-storing members.

Referring to FIG. 3, another prosthetic foot 210 is shown that can be similar in many respects to those described above. The foot 210 can include an upper forefoot portion 214, similar to those described above. The foot also can include either a lower footplate or a lower heel portion, similar to those described above. The forefoot portion 214 can include two or more portions, such as first and second portions 214a and b, disposed adjacent one another in a side-by-side relationship. The two portions 214a and b can be laterally separated by a gap. The two portions allow the forefoot portion to mimic the toe rotation of a natural foot. The first and second portions 214a and b can be independently movable with respect to one another. Because the foot 10 includes the two portions, the foot 10 is able to respond to uneven terrain more like a natural foot with rotating toes. In addition, the foot 10 is better able to simulate toe and axial foot rotation. The forefoot portion can be split along substantially the entire length. The footplate or heel portion can be similarly split. It is of course understood that the forefoot portion, footplate, and/or heel portion can be partially or wholly split. The first and second portions can be mirror images of one another, or can be configured to resemble an actual foot. In addition, the first and second portions can have different spring forces, or stiffness, to better simulate a natural foot.

Figure 4:
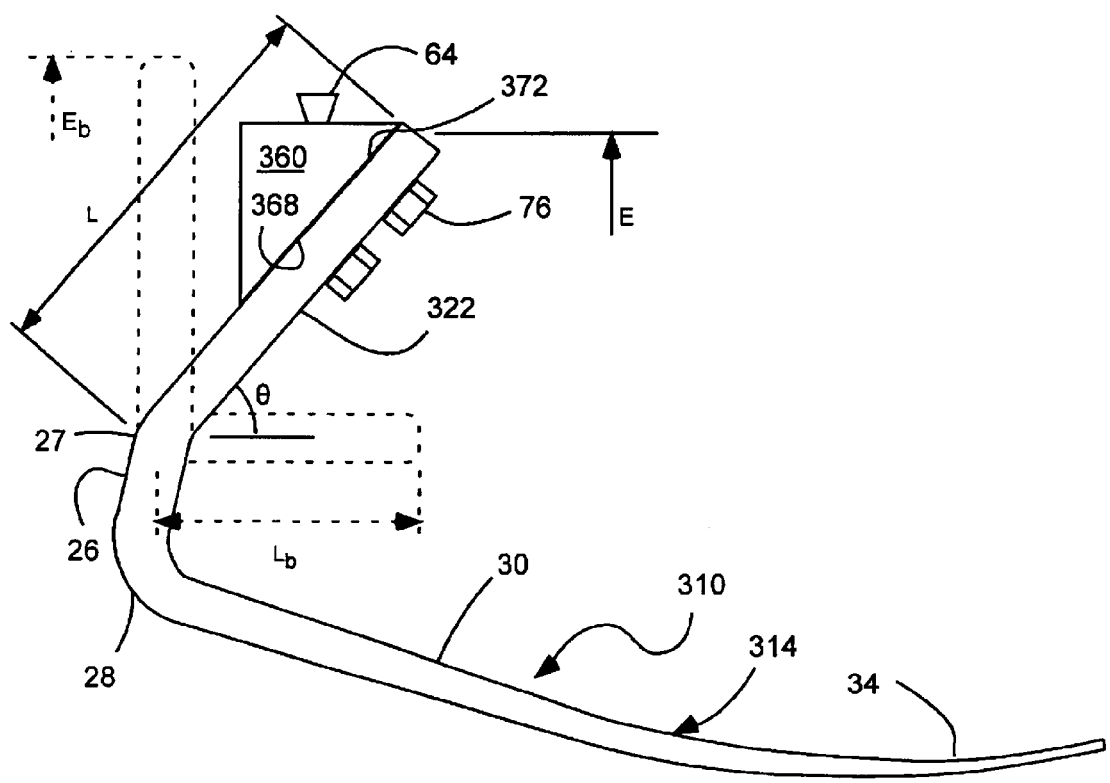
FIG. 4 is a side view of a prosthetic foot in accordance with an embodiment of the present invention.

Referring to FIG. 4, a prosthetic foot, indicated generally at 310, in accordance with the present invention is shown with an oblique attachment, or an attachment forming an oblique angle. The foot 310 can include an elongated, upper forefoot portion or forefoot 314 that is similar in many respects to those described above. In addition, the foot can include a lower footplate or a lower heel portion as described above. The attachment section 322 can be oblique, or can be disposed at an oblique angle. In addition, the attachment member 360 can include a lower oblique surface 368. The attachment section 322 of the upper forefoot portion 314 can include an upper oblique surface 372 that matches and attaches to the lower oblique surface 368. The attachment section 322 can be coupled to the attachment member 360 by fasteners, such as bolts 76. For example, the bolts 76 can extend through apertures in the attachment section 322 of the forefoot portion 314 and into threaded bores in the attachment member 360. It is of course understood that any type of fastener or connection can be used, including for example, screws, clips, etc.

The attachment section 322 of the upper forefoot portion 314, and the upper and lower oblique surfaces 372 and 368, are oblique or oriented at an oblique angle $\Theta$). In one aspect, the attachment section 322 can be oriented between approximately 20 and 70 degrees with respect to a horizontal axis. In another aspect, the attachment section 322 can be oriented between approximately 30 and 60 degrees with respect to a horizontal axis. In another aspect, the attachment section 322 can be oriented at approximately 45 degrees with respect to a horizontal axis, as shown. The attachment section 322 can extend upwardly and forwardly from the ankle section 326. Thus, the upper forefoot portion 14 extends rearwardly and downwardly through the attachment section 322.

The oblique angle of the attachment section 322 allows the attachment section 322 to extend a horizontal distance $L_b$ while having a longer length L. It will be appreciated that a horizontal attachment section, as shown in dashed lines, has a length $L_b$ that is relatively short compared to the length L of the attachment section 322. In addition, the oblique angle of the attachment section 322 allows the attachment section 322 to have a longer length L while extending to vertical elevation E. It will be appreciated that a vertical attachment section, as shown in dashed lines, with the same length extends to a relatively higher vertical elevation $E_b$ than the relatively lower vertical elevation E of the attachment section 322. Thus, the attachment section 322 can provide a longer lever arm while having a shorter vertical elevation. Thus, the attachment section 322 of the present invention extending at an oblique angle allows a longer length L without extending beyond a vertical elevation of a vertical attachment section of a J-shape. The longer length of the attachment section 22 allows extra length to store and return energy during use, contributes to extra spring or cushion of the foot, and improves vertical shock resistance.

The prosthetic feet disclosed above can be provided with the upper forefoot portion alone, without a lower footplate or heel portion.

Various aspects of such energy-storing prosthetic feet are shown and described in U.S. Pat. Nos. 5,944,760; 6,197,068; and 6,241,776, which are herein incorporated by reference.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A prosthetic foot device, comprising;
    an elongated forefoot portion having an upper attachment section configured to be coupled to a limb of an amputee, and extending 1) at least rearwardly through the attachment section, 2) downwardly and rearwardly through a first curved section, 3) downwardly through a discrete and straight ankle section positioned at a rearmost location of the foot device and oriented substantially vertically, 4) downwardly and forwardly through a second curved section , 5) forwardly through an arch section, and 6) forwardly to a toe section positioned at a toe location of a natural foot.

2. A device in accordance with claim 1, wherein the forefoot portion is flexible to store energy and resilient to return energy.

3. A device in accordance with claim 2, wherein the forefoot portion includes a composite material with fiber in a resin matrix.

4. A device in accordance with claim 1, further comprising:
    an attachment member, configured to be coupled to a limb of an amputee; and wherein the upper attachment section of the forefoot portion is attached to the attachment member.

5. A device in accordance with claim 1, further comprising:
    a lower footplate, attached to the forefoot portion, having a toe section positioned at a toe location of a natural foot, extending rearwardly through on arch section to a heel section positioned at a heel location of a natural foot.

6. A device in accordance with claim 5, wherein the toe section of the lower footplate is attached to the toe section of the elongated forefoot portion.

7. A device in accordance with claim 5, wherein the ankle section of the forefoot portion is positioned over the heel section of the lower footplate.

8. A device in accordance with claim 1, further comprising:
an elongated heel portion, attached to the forefoot portion, having an attachment section attached to the forefoot portion, and extending rearwardly to a heel section positioned at a heel location of a natural foot.

9. A device in accordance with claim 1, wherein the forefoot portion includes at least two laterally separated and adjacent forefoot portions.

10. A prosthetic foot device, comprising:
a) an attachment member, configured to be coupled to a limb of an amputee; and
b) an elongated forefoot portion having an upper attachment section attached to the attachment member, and extending at least rearwardly through the attachment section, downwardly through an ankle section, and forwardly through an arch section, to a toe section positioned at a toe location of a natural foot; and
c) the ankle section of the forefoot portion including a discrete, straight section positioned at a rearmost location of the foot device and oriented substantially vertically; and
d) the forefoot portion including a first curved section interconnecting the attachment section and the straight section, and a second curved section interconnecting the straight section and the arch section.

11. A device in accordance with claim 10, wherein the forefoot portion is flexible to store energy and resilient to return energy.

12. A device in accordance with claim 11, wherein the forefoot portion includes a composite material with fiber in a resin matrix.

13. A device in accordance with claim 10, further comprising:
a lower footplate, attached to the forefoot portion, having a toe section positioned at a toe location of a natural foot, extending rearwardly through an arch section to a heel section positioned at a heel location of a natural foot.

14. A device in accordance with claim 13, wherein the toe section of the lower footplate is attached to the toe section of the elongated forefoot portion.

15. A device in accordance with claim 13, wherein the ankle section of the forefoot portion is positioned over the heel section of the lower footplate.

16. A device in accordance with claim 10, further comprising:
an elongated heel portion, attached to the forefoot portion, having an attachment section attached to the forefoot portion, and extending rearwardly to a heel section positioned at a heel location of a natural foot.

17. A device in accordance with claim 10, wherein the forefoot portion includes at least two laterally separated and adjacent forefoot portions.

18. A device in accordance with claim 10, wherein the straight, discrete section has a length longer than at least one of the first and second curved sections.

19. A prosthetic foot device, comprising:
a) an attachment member, configured to be coupled to a limb of an amputee; and
b) an elongated forefoot portion having an upper attachment section attached to the attachment member, and extending at least rearwardly through the attachment section, downwardly through an ankle section, and forwardly through an arch section, to a toe section positioned at a toe location of a natural foot; and
c) the ankle section of the forefoot portion including an elongated, discrete, straight section positioned at a rearmost location of the foot device and oriented substantially vertically;
d) the forefoot portion including a first curved section interconnecting the attachment section and the straight section, and a second curved section interconnecting the straight section and the arch section; and
e) the elongated, discrete, straight section being longer than at least one of the first and second curved sections.

20. A device in accordance with claim 19, wherein the forefoot portion is flexible to store energy and resilient to return energy.

21. A device in accordance with claim 20, wherein the forefoot portion includes a composite material with fiber in a resin matrix.

22. A device in accordance with claim 19, further comprising:
a lower footplate, attached to the forefoot portion, having a toe section positioned at a toe location of a natural foot, extending rearwardly through an arch section to a heel section positioned at a heel location of a natural foot.

23. A device in accordance with claim 22, wherein the toe section of the lower footplate is attached to the toe section of the elongated forefoot portion.

24. A device in accordance with claim 22, wherein the ankle section of the forefoot portion is positioned over the heel section of the lower footplate.

25. A device in accordance with claim 19, further comprising:
an elongated heel portion, attached to the forefoot portion, having an attachment section attached to the forefoot portion, and extending rearwardly to a heel section positioned at a heel location of a natural foot.

26. A device in accordance with claim 19, wherein the forefoot portion includes at least two laterally separated and adjacent forefoot portions.

* * * * *